(12) United States Patent
Kim et al.

(10) Patent No.: US 9,974,932 B2
(45) Date of Patent: May 22, 2018

(54) METHOD AND SENSOR FOR DETECTING CATHETER OBSTRUCTION

(71) Applicants: Brian J. Kim, Los Angeles, CA (US); Ellis Meng, La Canada Flintridge, CA (US)

(72) Inventors: Brian J. Kim, Los Angeles, CA (US); Ellis Meng, La Canada Flintridge, CA (US)

(73) Assignee: University of Southern California, Los Angeles, CA (US)

(*) Notice: Subject to any disclaimer, the term of this patent is extended or adjusted under 35 U.S.C. 154(b) by 141 days.

(21) Appl. No.: 14/822,662

(22) Filed: Aug. 10, 2015

(65) Prior Publication Data

US 2016/0067464 A1 Mar. 10, 2016

Related U.S. Application Data

(60) Provisional application No. 62/046,424, filed on Sep. 5, 2014.

(51) Int. Cl.
*A61M 27/00* (2006.01)
*A61B 5/053* (2006.01)

(52) U.S. Cl.
CPC ......... *A61M 27/006* (2013.01); *A61B 5/0538* (2013.01)

(58) Field of Classification Search
CPC .................................... A61M 27/00–27/006
See application file for complete search history.

(56) References Cited

U.S. PATENT DOCUMENTS

| | | |
|---|---|---|
| 4,246,908 A | 1/1981 | Inagaki et al. |
| 4,593,703 A | 6/1986 | Cosman |
| 4,676,255 A | 6/1987 | Cosman |
| 5,026,348 A | 6/1991 | Venegas |
| 5,935,084 A | 8/1999 | Southworth |
| 6,248,080 B1 | 6/2001 | Miesel et al. |
| 6,533,733 B1 | 3/2003 | Ericson et al. |
| 8,088,091 B2 | 1/2012 | Thomas et al. |
| 8,457,733 B2 | 6/2013 | Linninger |
| 8,480,612 B2 | 7/2013 | Kassem |
| 2006/0020239 A1 | 1/2006 | Geiger et al. |
| 2009/0204019 A1 | 8/2009 | Ginggen et al. |
| 2012/0265028 A1 | 10/2012 | Hughes et al. |
| 2013/0102951 A1 | 4/2013 | Swoboda et al. |
| 2013/0109998 A1 | 5/2013 | Swoboda et al. |
| 2013/0245403 A1 | 9/2013 | Kassem |
| 2013/0247644 A1 | 9/2013 | Swoboda et al. |
| 2014/0171770 A1* | 6/2014 | Hann ............... A61B 5/00 600/324 |
| 2014/0276341 A1* | 9/2014 | Ludin ............... A61M 27/002 604/9 |

FOREIGN PATENT DOCUMENTS

WO WO 2010098868 A1 9/2010

\* cited by examiner

*Primary Examiner* — Benjamin Klein
(74) *Attorney, Agent, or Firm* — McDermott Will & Emery

(57) ABSTRACT

A self-monitoring catheter system may detect an obstruction during use of a catheter. The system may include a catheter with an interior lumen that has one or more ports into the lumen; a first and a second electrode; and an impedance measurement instrument that measures changes in the impedance between the first and the second electrodes after the first electrode is exposed to fluid within the catheter lumen, thereby signaling an obstruction during use of the catheter.

14 Claims, 5 Drawing Sheets

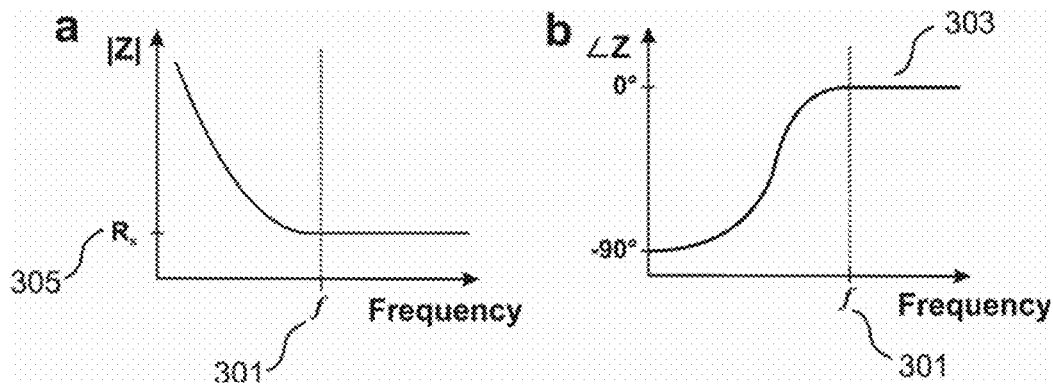
*FIG. 3A*  *FIG. 3B*
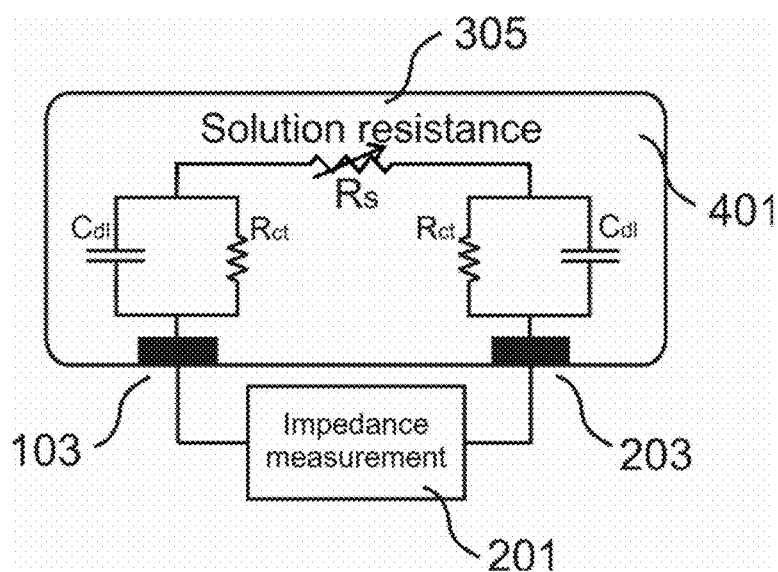
*FIG. 4*

METHOD AND SENSOR FOR DETECTING CATHETER OBSTRUCTION

CROSS-REFERENCE TO RELATED APPLICATION

This application is based upon and claims priority to U.S. provisional patent application 62/046,424, entitled "METHOD AND SENSOR FOR DETECTING CATHETER OBSTRUCTION," filed Sep. 5, 2014. The entire content of this application is incorporated herein by reference.

STATEMENT REGARDING FEDERALLY SPONSORED RESEARCH

This invention was made with government support under Grant No. EFRI-1332394 awarded by the National Science Foundation. The government has certain rights in the invention.

BACKGROUND

Technical Field

This disclosure relates to catheter obstructions.

Description of Related Art

Hydrocephalus is a condition characterized by excessive accumulation of cerebrospinal fluid (CSF) in the brain and a corresponding increase in intracranial pressure (ICP)

Hydrocephalus has been treated using implanted CSF shunts. CSF shunts can restore hydrodynamic balance by increasing CSF outflow to normalize ICP and improve symptoms. 70-80% patients with shunts improve postoperatively.

A shunt can include a ventricular (proximal) catheter, a valve mechanism, and a distal catheter. Peritoneum placement of the distal catheter is common, with other locations including the pleura, ureter, bladder, and vascular spaces.

Various shunts have been introduced, but can create complications due to inadequate shunt performance, such as obstruction of a catheter used in the shunt.

Implanted and external sensors exist to dynamically measure shunt flow [M. Geiger and L. Speckman, "Cerebral spinal fluid flow sensing device," US 20060020239, 2006; S. Kassem, "Wireless flow sensor," US 20130245403 A1, 2013; M. Swoboda, et al. "CSF shunt flow enhancer, method for generating CSF flow in shunts and assessment of partial and complete occlusion of CSF shunt systems," US 20130102951 A1, 2013; M. Swoboda, et al. "Real time flow measurement system & method/" US 20130109998 A1, 2013] and pressure [E. R. Cosman, "Telemetric differential pressure sensor with the improvement of a conductive shorted loop tuning element and a resonant circuit," U.S. Pat. No. 4,593,703 A, 1986; E. R. Cosman, "Telemetric in-vivo calibration method and apparatus using a negative pressure applicator," U.S. Pat. No. 4,676,255 A, 1987; M. N. Ericson, et al., "Implantable device for in-vivo intracranial and cerebrospinal fluid pressure monitoring," U.S. Pat. No. 6,533,733 B1, 2003; A. Ginggen and Y. Tandy, "Combined pressure and flow sensor integrated in a shunt system," US 20090204019 A1, 2009; K. Hughes and A. Strachan, "Sensor, circuitry, and method for wireless intracranial pressure monitoring," US 20120265028 A1, 2013; I. Igarashi et al. "Intracranial pressure transducer," U.S. Pat. No. 4,246,908 A, 1981; S. Kassem, "Wireless shunts with storage," U.S. Pat. No. 8,480,612 B2, 2009; K. A. Miesel and L. Stylos, "Intracranial monitoring and therapy delivery control device, system and method," U.S. Pat. No. 6,248,080 B1, 2001; C. B. Southworth, "Inflatable pressure indicator," U.S. Pat. No. 5,935,084 A, 1999; M. Swoboda, et al., "Implantable pressure sensor," US 20130247644 A1, 2013; G. A. Thomas, et al., "No clog shunt using a compact fluid drag path," U.S. Pat. No. 8,088,091 B2, 2012; J. G. Venegas, "Apparatus and method for the detection of IV catheter obstruction and extravasation," U.S. Pat. No. 5,026,348 A, 1991]. However, catheter obstruction may need to be inferred based on observed patterns of flow or pressure. This may be inefficient and can lead to false positives or negatives, as these measures are not direct measurements of patency.

Optical methods have been used to monitor movement of specific particles within CSF through fluidic channels. These optical methods provide feedback on applying a stimulus pulse between electrodes oriented in a similar design as this disclosed technology. [R. G. Dacey, et al., "Systems, devices, and methods including infection-fighting and monitoring shunts," WO 2010098868 A1, 2010.]

Another approach involves measurement of electrochemical impedance within a hydrocephalic shunt environment as an indirect means of inferring volume of the CSF within the ventricles, which can be more accurate for determining CSF dynamics than pressure or flow [A. Linninger, "Monitoring and controlling hydrocephalus," U.S. Pat. No. 8,457,733 B2, 2010]. However, this sensor system may not detect obstruction events of the catheter and instead may be used only to diagnose hydrocephalus.

Commercial sensor systems are being developed by Integra LifeSciences (Integra Camino), Transonic Systems, Aesculap (Meithke), and Issys. However, these sensors may use transduction principles and single time point measurements that provide a snapshot of CSF dynamics. However, they may not have the capability for multiple measurements over time, which is necessary to monitor progressive obstruction. Some may also monitor flow indirectly and may not provide quantitative measurement of patency or obstruction.

SUMMARY

A self-monitoring catheter system may detect an obstruction during use of a catheter. The system may include a catheter with an interior lumen that has one or more ports into the lumen; a first and a second electrode; and an impedance measurement instrument that measures changes in the impedance between the first and the second electrodes after the first electrode is exposed to fluid within the catheter lumen, thereby signaling an obstruction during use of the catheter.

The first electrode may be within the catheter lumen.

The second electrode may or may not be within the catheter lumen.

The self-monitoring catheter system may include a living body having exterior skin. The catheter may be within the living body. The second electrode may be on the skin or within the living body.

The self-monitoring catheter system may include a hydrocephalus shunt or extraventricular drain that shunts fluid within the catheter.

The first and/or second electrode may be affixed to a polymer substrate.

The polymer substrate may be within the catheter lumen.

The polymer substrate may be made of Parylene C.

The impedance measurement instrument may apply an AC signal across the electrodes at frequency within the range of 1 to 50 kHz.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIGS. 3A and 3B illustrate examples measurements of impedance vs frequency obtained during electrochemical impedance spectroscopy measurements. FIG. 3A illustrates an example of impedance magnitude vs frequency, while FIG. 3B illustrates an example of impedance phase vs frequency.

FIG. 4 illustrates an example of an equivalent circuit model of two electrodes in an electrolyte.

FIG. 7A illustrates the device adjacent to a fluid line, FIG. 7B illustrates the device in-line with a fluid line, and FIG. 7C illustrates the device built into a shunt/catheter system.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Electrochemical impedance and an electrochemical impedance-based sensor may be used in detecting progressive obstruction or complete blockage of implanted drainage catheters. Such catheters may be placed in a brain ventricle for draining excess cerebrospinal fluid in the treatment of hydrocephalus. They may instead be placed within a cardiovascular system, endocrine system, lymphatic system, digestive system, or any other fluidic system of the body for fluid removal and/or for identifying an obstruction. Diameters of these catheters, as well as their subsequent drainage ports can vary in size depending on the application and may, for example, measure up to 1 cm; the sensor can, for example, be utilized for any catheter or port size up to 1 cm.

To provide a quantitative, transient measurement of the blockage of the drainage ports in such catheters, a patency sensor was developed that utilizes the measurement of electrochemical impedance between a set of metal thin film electrodes placed in key regions of interest. Because of the thin film construction and simple transduction method for patency, this method and sensor can be used for a broad spectrum of catheter patency diagnosis applications for any fluidic drainage interface (e.g. intravascular, intraocular, intra-abdominal, etc.). Because of the obstruction sensing method, the sensor response may not be affected by patient orientation; this may allow for transient measurements while the sensor is implanted, regardless of patient position (i.e. standing or lying down, known to cause issues with pressure and flow sensors).

Figure 1:
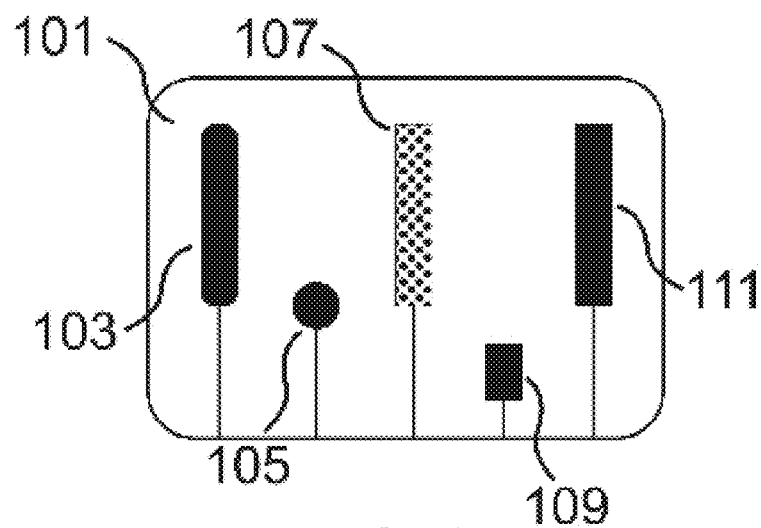
FIG. 1 illustrates an example of a polymer-based sensor device with electrodes.

FIG. 1 illustrates an example of a polymer-based sensor device with electrodes. As illustrated in FIG. 1, the sensor may be constructed on a polymer substrate 101 using standard surface micromachining of polymer layers and may include one or more electrodes, such as electrodes 103, 105, 107, 109, and 111. The sensor may use polymers typically used for microfabrication, such as Parylene C and/or polyimide. Alternatively, the substrate may be any non-conductive material with suitable properties for contact with biological fluids and tissue. The electrodes may be made of conductive material(s) typically used for electrode implants, such as platinum, gold, titanium, and/or iridium oxide. The electrodes can be any shape, such as any of the various shapes illustrated in FIG. 1. The electrodes may be of any size, such as any size that can be reliably fabricated onto a polymer substrate and incorporated within current catheter systems, ranging from 100 $\mu m^2$ to 1 $mm^2$. A conductive coating 107 may be applied to an electrode to increase its surface area (and thus sensing performance of the devices), such as PtIr and/or PEDOT. Biocompatible materials may be chosen for one or more of the electrodes for improved performance in vivo. A polymer-based flat flexible cable and contact pad array for electrical connection may be incorporated into the design to allow for connections to an impedance measurement instrument.

At least two electrodes may be used for sensing. The electrode sites may vary, depending on the area of interest for specific types of blockage.

Figures 2A, 2B:
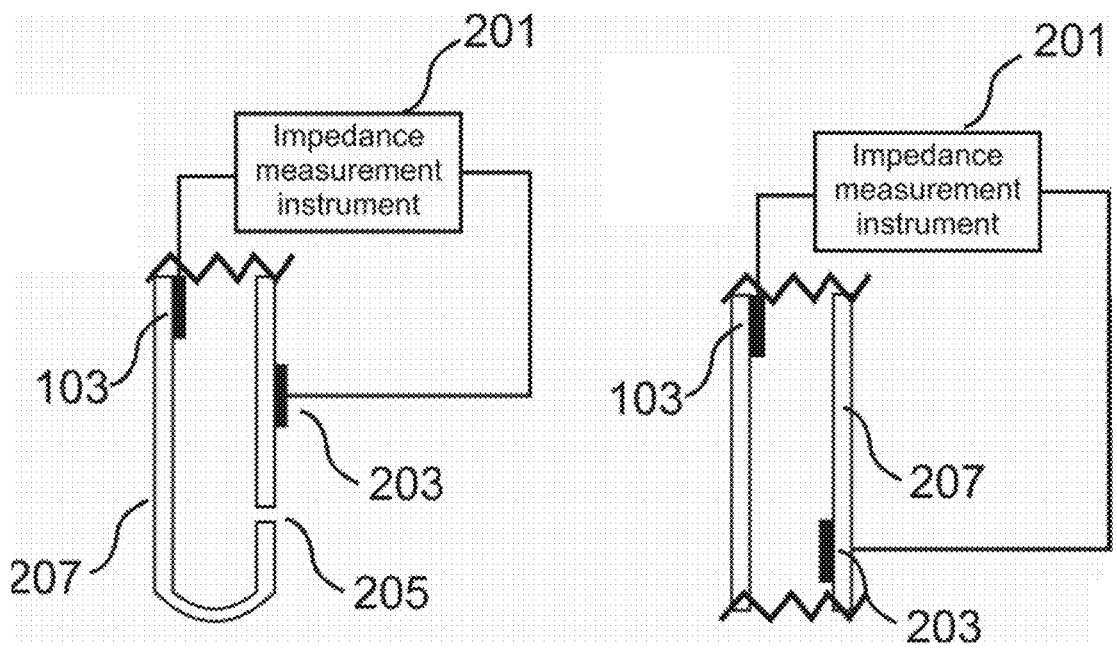
FIGS. 2A and 2B illustrate examples of electrodes in different configurations with respect to a catheter. Those in FIG. 2A may assess an obstruction on an external surface of a catheter and/or in one or more ports into the lumen, while those in FIG. 2B may assess an obstruction in the lumen of the catheter.

FIGS. 2A and 2B illustrate examples of electrodes 103 and 203 in different configurations with respect to a catheter 207. Those in FIG. 2A may assess a superficial obstruction on an external surface of the catheter 207 and/or one or ports into the lumen, while those in FIG. 2B may assess an obstruction in the lumen of the catheter 207. To assess superficial blockages (i.e. obstruction phenomenon covering fluidic ports of a catheter), at least one electrode 103 in FIG. 2A may be placed within the lumen of the catheter 207 in contact with fluid inside the catheter 207. At least one other electrode 203 in FIG. 2A may be placed exterior to the lumen and ports of the catheter (i.e. outer electrode) 207 such that a fluidic port 205 of the catheter 207 act as a fluidic via between the electrode 103 within the catheter 207 and the electrode 207 outside of the catheter 207. Variations of this outer electrode placement may include on an external surface of the catheter or other locations external to the lumen and ports of the catheter that provide an electrical/electrochemical path between the outer electrode and the inner electrode(s). For example, the outer electrode could be placed on the skin or in a remote tissue or body cavity. Thus, this outer electrode need not necessarily be attached to a polymer-based sensor. Embodiments of the outer electrode may include any invasive (e.g. microelectrodes, needle electrodes) or noninvasive electrode (e.g. surface electrodes, patch electrodes) placed within or on the patient. Impedance may be measured between an electrode within the catheter 207 lumen and an electrode outside of the catheter 207 lumen.

FIG. 2B illustrates another embodiment to assess blockages of a catheter lumen. In this embodiment, electrode 103 may again be placed within the catheter 207 such that it is in-line with fluid flow within the catheter 207, and electrode 203 may also be placed within the catheter 203, again within the fluid flow. The electrodes may be placed anywhere inside of the catheter 207 within the fluid flow, such as on an inner wall and/or on opposing inner sides. The electrode(s) can be placed anywhere along the length of the catheter. In this embodiment, impedance may be measured between the two internal electrodes to assess shunt lumen blockage.

The electrochemical impedance of the solution spanning between the two (or more) immersed electrodes may be monitored. Impedance can be measured using an impedance measurement instrument 201, such as a high precision LCR meter, handheld LCR meter, impedance analyzer, network analyzer, or spectrum analyzer. The impedance measurement instrument may instead infer impedance from a measurement of voltage, such as by using a voltage divider in a Wheatstone bridge. For these measurement devices, a low frequency (typically in the 1-50 kHz range) AC voltage may be applied across the electrodes and the amount of current drawn may be measured by the impedance measurement instrument 201.

FIGS. 3A and 3B illustrate examples of measurements of impedance vs frequency obtained during electrochemical impedance spectroscopy measurements. FIG. 3A illustrates an example of impedance magnitude vs frequency, while FIG. 3B illustrates an example of impedance phase vs frequency. To find an optimal measurement frequency for patency detection, electrochemical impedance spectroscopy measurements may be taken, where the impedance magnitude and phase of the system are measured across a range of frequencies. A frequency 301 in a region 303 where the phase reaches a plateau at 0° may be chosen.

FIG. 4 illustrates an example of an equivalent circuit model of two electrodes in an electrolyte. At the desired measurement frequencies, the impedance response may be dominated by solution resistance 305 per the Randle's equivalent circuit model for electrodes 103 and 203 in an electrolyte solution, modeled in the figure as a block 401. The voltage may be low enough (depending on the electrode material) such that only reversible chemical reactions are present and the solution is not chemically modified during the measurement process. This measurement may consume very low power, such as requiring only nW-μW (1-100 mV, 1-100 nA).

During a shunt's implanted lifetime, tissue and other biological material may amass and obstruct the holes/lumen of the catheter over time. This may disturb the fluidic conduction path between outer and inner electrodes. With blockage of the holes/lumen, the electrochemical impedance may correspondingly increase due to an increase in the solution resistance. The mechanism that causes the change in solution resistance may depend on the specific obstruction; obstruction occurrences can alter the (1) ρ, resistivity of the solution (i.e. ionic concentration of the solution) between the measurement electrodes, (2) A, the cross sectional area between the electrodes, and/or (3) l, the distance between the electrodes to cause a change in the measured solution resistance, as illustrated by the following Equation 1:

$$Z \approx R_S = \frac{\rho l}{A}; \text{ for sufficiently high } f_{meas} \quad (1)$$

The sensor may be capable of tracking progressive and/or blocked catheter states using this method.

Figure 5:
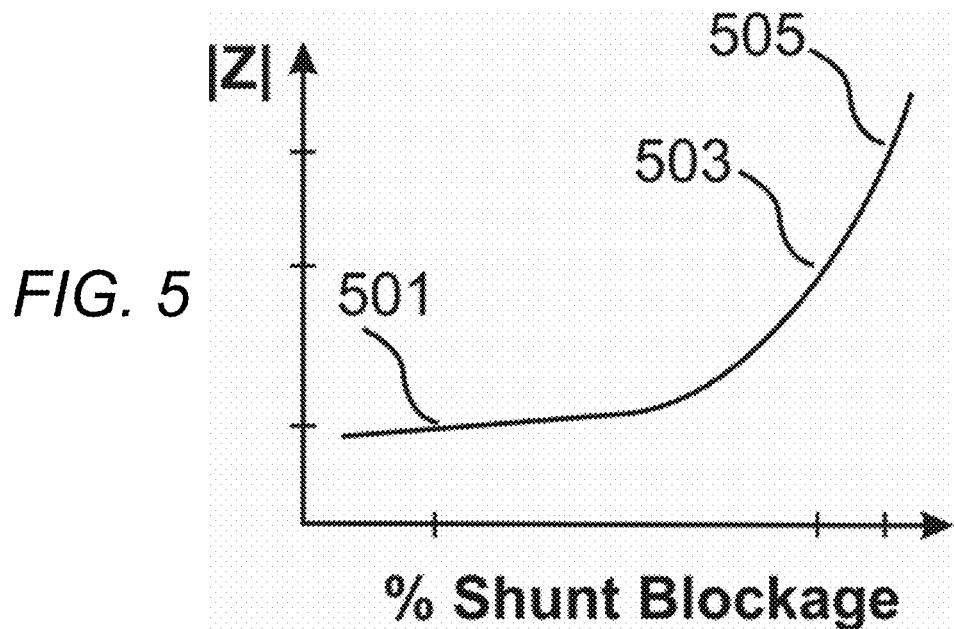
FIG. 5 illustrates an example of a plot diagram of a relationship between percent shunt blockage and sensor impedance magnitude.

FIG. 5 illustrates an example of a plot diagram of a relationship between percent shunt blockage and sensor impedance magnitude. As illustrated in FIG. 5, numerous measurements may reveal a relationship between measured impedance and percent shunt blockage. By comparing a measured impedance value with this chart, the degree of shunt blockage can be assessed. This may automatically be done by a computer system that includes data representative of what is shown in FIG. 5 or a mathematical relationship that substantially tracks what is shown in FIG. 5. The correlation between measured impedance and percent shunt blockage may follow an increasing trend, with low percent shunt blockage corresponding to small deviations from a baseline 501, and increasing to higher impedance changes 503 and then 505 for increase percent shunt blockage.

Figure 6:
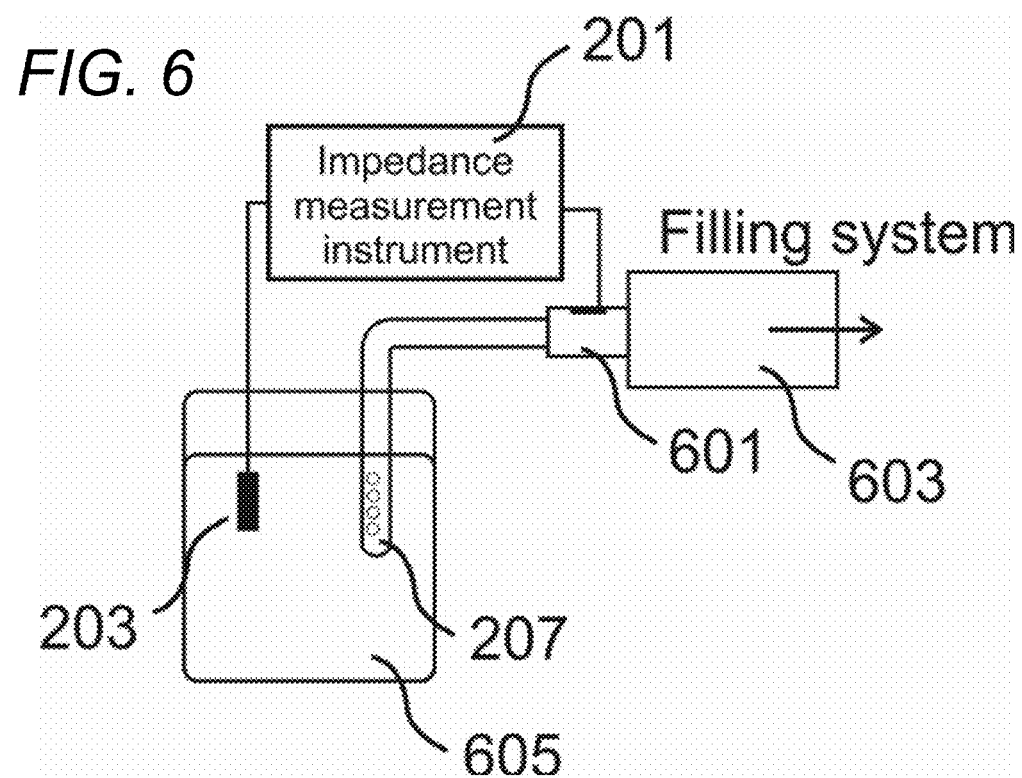
FIG. 6 illustrates an example of a benchtop testing setup for sensor characterization.

FIG. 6 illustrates an example of a benchtop testing setup for sensor characterization. An actual benchtop calibration of a system included a mock silicone catheter (1.5 mm inner diameter) 207 that modeled obstructed catheters by varying the numbers of open holes (1 mm diameter), with 16 holes simulating 100% open (a 4-holed catheter might be classified as 75% blockage, 8 holes as 50%, etc.). A catheter was then placed within a beaker of CSF 605 [ionic formulation for 1 L of DI water: 8.66 g NaCl, 0.224 g KCl, 0.206 g $CaCl_2.2H_2O$, 0.163 g $MgCl_2.6H_2O$, 0.214 g $Na_2HPO_4.7H_2O$, 0.027 g $NaH_2PO_4.H_2O$] and connected to a sensor module 601 using a 1/16" barb-to-luer connector. The assembly was filled via a syringe or peristaltic pump 603 (for static and flow conditions, respectively) prior to testing. A platinum wire electrode 203 was placed within the beaker to close the circuit and complete the sensing setup and act as the external electrode. Device calibration was completed by measuring the impedance between the modeled set of electrodes with varying mock catheters using a high precision LCR meter or any impedance measurement instrument 201. Experiments with the sensor indicated that sensor performance may remain consistent, regardless of variation in flow (0.03-0.6 mL/min) or variation in temperature (e.g., from 32-44° C.). The sensor may also be capable of functioning following sterilization using $H_2O_2$ plasma.

Figure 7A:
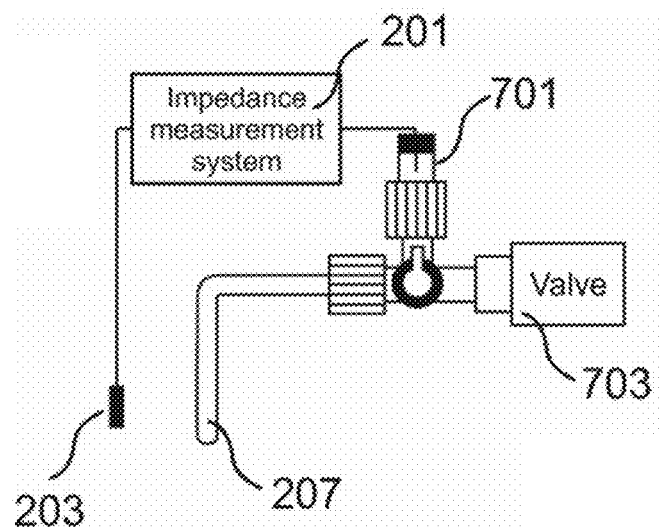
FIGS. 7A-7C illustrate examples of device orientations for integration with current shunt/catheter systems.
Figure 7B:
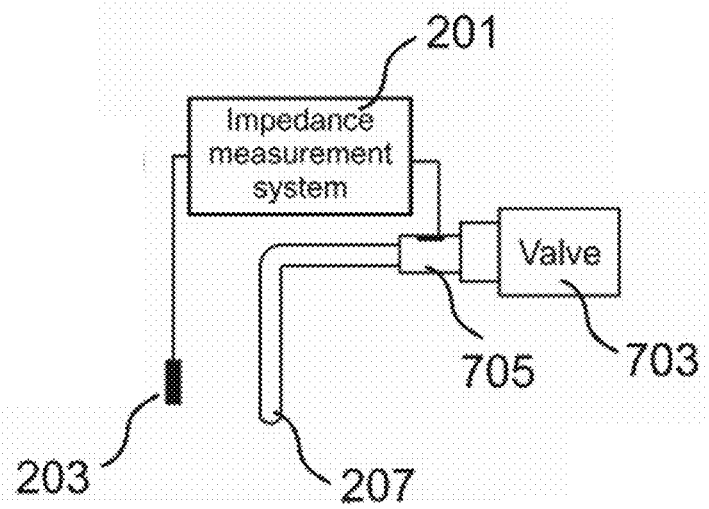
Figure 7C:
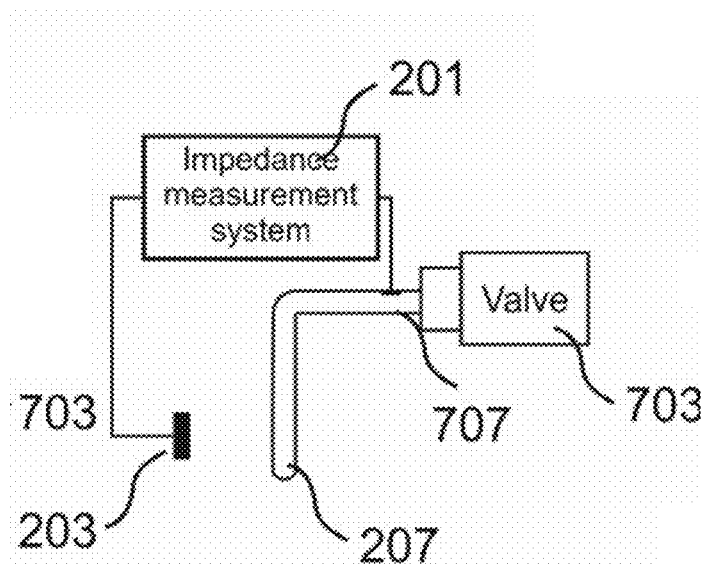

FIGS. 7A-7C illustrate examples of device orientations for integration with current shunt/catheter systems. FIG. 7A illustrates the device adjacent to a fluid line, FIG. 7B illustrates the device in-line with a fluid line, and FIG. 7C illustrates the device built into a shunt/catheter system. As illustrated in these figures, this sensor may be easily integrated with current shunt technologies 703 (which may include a valve) because of the polymeric, open architecture construction of the sensor.

In one embodiment, the sensor can be integrated into the catheter, such that it is a part of a shunt system 707.

The sensor may be constructed directly in the catheter during its manufacturing. The sensor may also be placed within the catheter system via an opening made or built into any pre-manufactured catheter. Adhesives may be used to secure the sensor in place within the catheter.

In another embodiment, the sensor can be placed in a stand-alone packaging system as a modular add-on to current shunt systems 703 that can be attached and removed. In this embodiment, variations may include packaging modules where the sensor sits in-line with fluid flow 705, or where the sensor sits adjacent to a fluid path 701.

The sensor may be placed within the modules via a slit or aperture that allows for the sensor to be curled around the inner lumen of the module or placed directly within the fluid-line and therefore, the fluid path. Adhesives may be used to secure the sensor in place within the module.

The system may be implanted within a body.

Figure 8A:
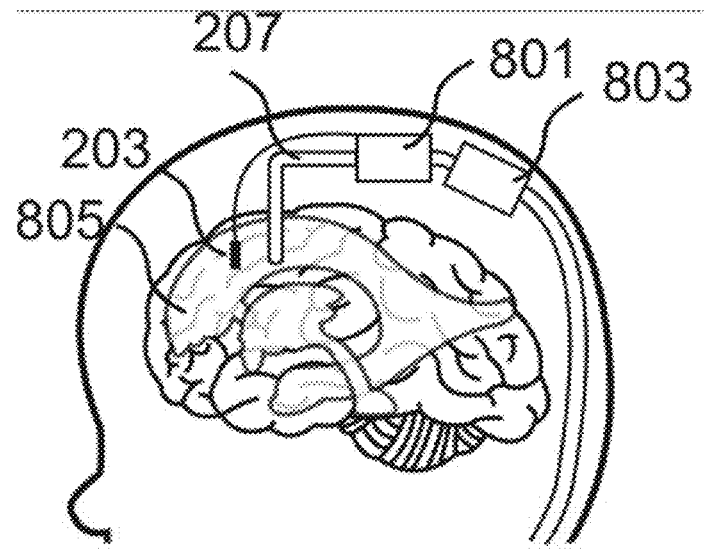
FIG. 8A illustrates an example of a sensor implanted within a head of patient.
Figure 8B:
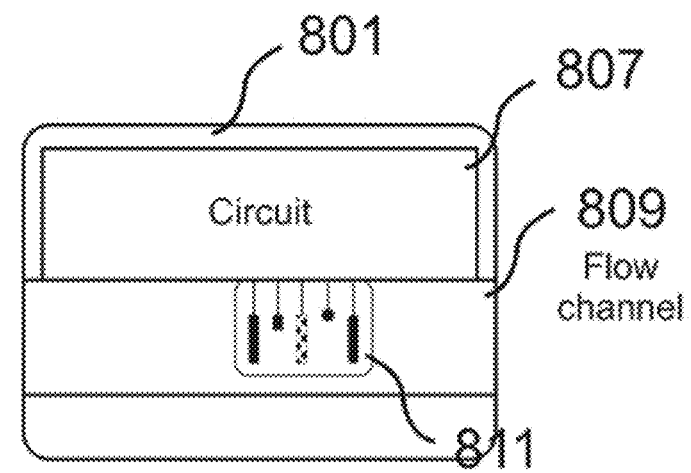
FIG. 8B illustrates the sensor in an example of packaging.
Figure 8C:
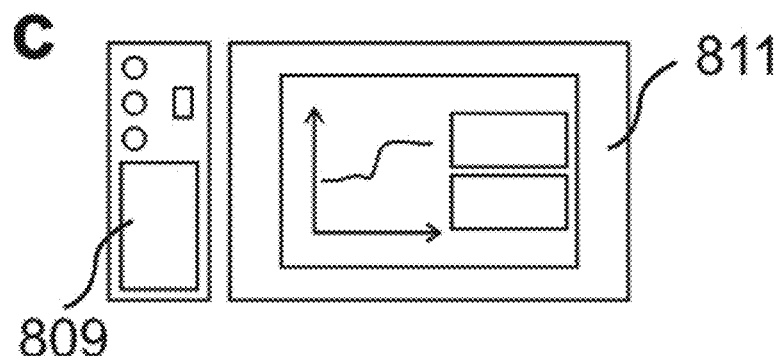
FIG. 8C illustrates a console and graphical user interface that displays sensor readings to a physician.

FIG. 8A illustrates an example of a sensor implanted within a head of patient. FIG. 8B illustrates the sensor in an example of packaging. A modular add-on 801 can be used to contain the sensor either in-line or adjacent to fluid flow, while allowing for connection between the catheter 207 to the rest of the shunt system, which may include a valve and distal catheter system 803. If the sensor is in-line with fluid flow, the sensor 811 may sit within a flow channel 809 within the modular add-on 801. Another embodiment of the system can have the sensor integrated into an existing catheter or shunt system with the electronics protected in another package. The module can also contain electronics 807 that may be used for impedance measurement, wireless data transmission, and/or wireless power transmission to power the implanted system. The external electrode(s) in this case can be similar to any of the electrodes discussed above and be part of the system or external to the system. The data may be transmitted to a console unit 809 that would connect to a computer to provide sensor readout via a graphical user interface 811.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

For example, electrodes need not be constructed onto a separate module, but can be directly fabricated as part of the catheter. Electrodes need not be microfabricated using thin film metals but can instead be bulk metal electrodes, such as wire or discs. Instead of impedance measurements, resistance or capacitance measurements can be used to approximate a similar value as a measurement of obstruction. Implantable devices may have wired connectors or ports instead of wireless data transmission schemes.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A self-monitoring catheter system for detecting an obstruction during use of a catheter comprising:
   a catheter with an interior lumen that has one or more ports into the lumen;
   a first and a second electrode; and
   an impedance measurement instrument that measures and signals changes in the impedance between the first and the second electrodes that is caused by an obstruction during use of the catheter after the first electrode is exposed to fluid within the catheter lumen,
   wherein the first or the second electrode is affixed to a polymer substrate within the catheter lumen.

2. The self-monitoring catheter system of claim 1 wherein the first electrode is within the catheter lumen.

3. The self-monitoring catheter system of claim 2 wherein the second electrode is within the catheter lumen.

4. The self-monitoring catheter system of claim 2 wherein the second electrode is not within the catheter lumen.

5. The self-monitoring catheter system of claim 4 wherein:
   the catheter is configured to be positioned within a living body; and
   the second electrode is configured to be positioned on an exterior skin of the living body.

6. The self-monitoring catheter system of claim 2 wherein the catheter and the second electrode are configured to be positioned within a living body.

7. The self-monitoring catheter system of claim 1 further comprising a hydrocephalus shunt or extraventricular drain that shunts fluid within the catheter.

8. The self-monitoring catheter system of claim 1 wherein the first electrode is affixed to a polymer substrate.

9. The self-monitoring catheter system of claim 8 wherein the polymer substrate is within the catheter lumen.

10. The self-monitoring catheter system of claim 9 wherein the polymer substrate is made of Parylene C.

11. The self-monitoring catheter system of claim 8 wherein the second electrode is affixed to the polymer substrate.

12. The self-monitoring catheter system of claim 11 wherein the polymer substrate is within the catheter lumen.

13. The self-monitoring catheter system of claim 12 wherein the polymer substrate is made of Parylene C.

14. The self-monitoring catheter system of claim 1 wherein the impedance measurement instrument applies an AC signal across the electrodes at frequency within the range of 1 to 50 kHz.

\* \* \* \* \*